United States Patent [19]

Meyer

[11] 4,016,423
[45] Apr. 5, 1977

[54] INFRARED ANALYZER OF CONSTANT RADIANT ENERGY

[75] Inventor: Emilio G. Meyer, Rozzano (Milan), Italy

[73] Assignee: Leeds & Northrup Italiana S.p.A., Milan, Italy

[22] Filed: Jan. 20, 1976

[21] Appl. No.: 650,748

[30] Foreign Application Priority Data

Feb. 4, 1975 Italy ................................. 19938/75

[52] U.S. Cl. .............................. 250/343; 250/205; 250/210; 250/349

[51] Int. Cl.[2] ...................... G01J 1/00; G01J 1/32; G01N 21/24; G01N 21/26

[58] Field of Search .......... 250/355, 205, 210, 349, 250/343, 209

[56] References Cited

UNITED STATES PATENTS

| | | | |
|---|---|---|---|
| 2,775,160 | 12/1956 | Foskett et al. | 250/343 |
| 3,601,613 | 8/1971 | Hock | 250/205 |
| 3,911,277 | 10/1975 | Cederstrand et al. | 250/343 |

*Primary Examiner*—Alfred E. Smith
*Assistant Examiner*—T. N. Grigsby
*Attorney, Agent, or Firm*—Diller, Brown, Ramik & Wight

[57] ABSTRACT

This invention relates to an improved infrared analyzer, wherein the total radiant energy reaching the detector is maintained at a constant value independently from the aging of the source of radiant energy or the soiling of the sample cell. According to the invention, the improved infrared analyzer comprises a comparator, whose outlet feeds the radiant energy source and whose inlets receive a reference signal of constant value and, respectively, a signal which varies as a function of the total radiant energy received and measured by the detector.

3 Claims, 1 Drawing Figure

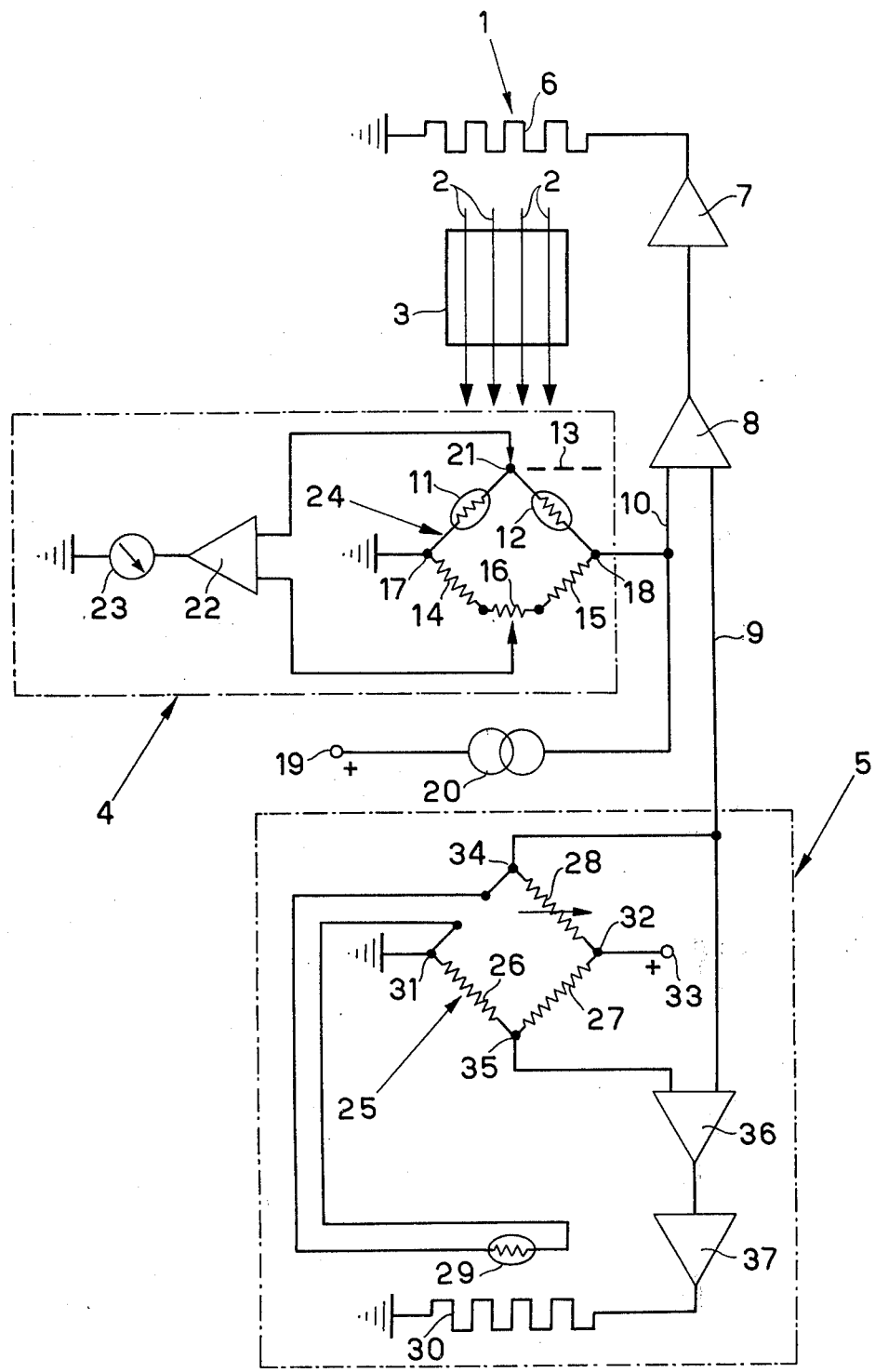

INFRARED ANALYZER OF CONSTANT RADIANT ENERGY

This invention relates to a new improved infrared analyser, wherein the total radiant energy reaching the detector is maintained at a constant value.

Infrared analysers used for determining the presence and concentration of a specific component in a liquid or gaseous sample generally comprise a source of radiant energy arranged to direct an infrared radiation beam against the sample to be analysed, and a detector arranged to receive said radiation beam downstream of the sample and provide a measurement of the concentration of the component under investigation in the form of an indication of the quantity of energy of infrared frequency absorbed by the said component during passage of the radiation beam through the sample. Detectors for analysers of the aforementioned type generally comprise two thermistors both exposed to the radiation from the sample under analysis, in the case of one of them by way of screening means arranged to produce a different ohmic response by the two thermistors when energy is absorbed by the investigated component in the sample under analysis (a particularly suitable screening means is the optical filter described and claimed in the copending patent application of the same applicant No. 624,654 filed on Oct. 22, 1975). This difference in response has the effect of producing a more or less accentuated unbalance (according to the concentration of the component) in an electrical bridge circuit of which said thermistors form part, with the result that the indication of the extent of this unbalance, obtained by a suitable measuring instrument, constitutes a measurement of the quantity of energy absorbed by the component under investigation, and therefore by implication a measurement of the concentration of this component in the sample under analysis.

For the results supplied by analysers of the aforementioned type to be completely trustworthy and constant with time, the total radiant energy reaching the detector must notably not vary with time with changing conditions, such as atmospheric conditions or aging of the source. This is a problem which has already been solved with regard to the influence of temperature, but has not been solved from other aspects such as the influence of aging of the source of radiant energy or the influence of the various levels of soiling of the cell containing the sample to be analysed.

The object of the present invention is to provide an infrared analyser in which the radiant energy reaching the detector is maintained at a constant value independently of the aging of the source or the soiling of the sample cell.

This object is attained according to the invention by an infrared analyser of the aforementioned general type, wherein the source of radiant energy is fed by the outlet of a comparator which receives as its respective inlets a reference signal of constant value and a signal which varies as a function of the sum of the instantaneous ohmic values of the two thermistors and therefore as the total radiant energy received by the detector.

Thus, if through aging or soiling, the radiant energy received by the detector tends to diminish and therefore reduce the detecting capacity and sensitivity of the analyser, this reduction in radiant energy is sensed by the two thermistors and gives rise to a signal representing the total energy received, which when compared with the aforementioned reference signal produces a signal representing the feed from the source of radiant energy which in its turn becomes varied in such a manner as to increase the radiant energy transmitted to an extent corresponding to the sensed reduction in the radiant energy received. This latter may therefore be maintained fundamentally constant with time and consequently the response of the analyser may be maintained constantly trustworthy and reproducible, independently of any source aging or soiling of the sample cell.

The characteristics of the present invention, together with the aforementioned and other further advantages deriving from it, will be more evident from the detailed description given hereinafter of a preferred embodiment illustrated diagrammatically by way of example in the accompanying drawing.

The analyser shown on the drawing comprises fundamentally a source of radiant energy 1 of infrared frequency arranged to direct a radiation beam 2 against a sample cell 3 containing the sample to be analysed, a detector 4 arranged to receive said radiation beam downstream of the sample cell and provide a measurement of the investigated component in the sample under analysis in the form of an indication of the quantity of energy of infrared frequency absorbed by said component during the passage of said radiation beam through the sample cell, and a temperature controller 5 arranged to maintain the temperature of the environment in which the analyser operates constant.

The radiant energy source 1 consists in fact of an electrical resistance 6, supplied by two amplifiers 7 and 8 the first of which is a power amplifier and the second a differential amplifier which acts as a comparator between a constant reference signal 9 supplied by the temperature controller 5 and a variable signal 10 supplied by the detector 4 as a function of the total radiant energy received at any moment by the detector.

The detector 4 is of the type described in the aforementioned patent application and comprises fundamentally two thermistors 11 and 12 of negative thermal coefficient, both of which are exposed to the radiation beam emerging from the sample cell 3, in the case of the second of them by way of an optical interference filter 13 arranged to pass only a restricted band of frequencies lying within the range of the infrared frequencies absorbed by the investigated component in the sample under analysis. The two thermistors 11 and 12 are connected into an electrical Wheatstone Bridge circuit 24, which also comprises two fixed resistors 14 and 15 and a potentiometer 16, and has one node 17 connected to earth and the opposite node 18 connected to a positive terminal 19 by way of a constant current transformer 20. A third node 21 between the two thermistors 11 and 12 and the slider of the potentiometer 16 are connected to the two inlets of a differential amplifier 22, a measuring instrument 23 being connected between the outlet thereof and earth to visually indicate the extent of any unbalance of the bridge.

The temperature controller 5 comprises an electrical Wheatstone Bridge circuit 25 with its four branches formed by two fixed resistors 26 and 27, a variable resistor 28 and a thermistor 29 which acts as a thermal sensor for an electrical heating element 30 which heats the environment in which the analyser operates. Two opposing nodes 31 and 32 of the bridge 25 are connected to earth and a positive terminal 33 respectively, while the other two nodes 34 and 35 are connected to two inlets of a differential amplifier 36, the outlet of which supplies the heating element 30 by way of a power amplifier 37. The reference signal 9 for the comparator 8 is also taken from the node 34.

The analyser shown on the drawing operates as follows. Besides keeping ambient temperature constant by the control exercised by the bridge 25 and differential amplifier 36 on the feed current for the heating element 30, the temperature controller 5, by way of the amplifiers 8 and 7, also supplies the radiant energy source 1 with a constant feed current which causes emission of a determined quantity of infrared energy by the source 1.

If a sample cell 3 in which a determined component is to be investigated is placed between the source 1 and detector 4, certain of the frequencies which make up the emitted radiant energy are absorbed by this component, because of which the ohmic response of the thermistor 12 protected by the filter 13 is substantially changed, while there is practically no change in the response of the unprotected thermistor 11. The bridge 24 therefore suffers an unbalance, which is amplified by the amplifier 22 and detected by the measuring instrument 23 which indicates the quantity of energy of infrared frequency absorbed by the investigated component in the sample under analysis and, as a function thereof, the concentration of this component in said sample.

The total quantity of radiant energy reaching the detector 4 is maintained constant independently of any phenomena which tend to reduce it (such as aging of the source or any soiling of the sample cell) by the feedback provided by the connection between the node 18 of the bridge 24 and the second inlet of the comparator 8. This connection means that a continuous comparison is made between the fixed reference signal 9 and a variable signal 10 which, consisting of the voltage between the nodes 18 and 17 and consequently the voltage across the two thermistors 12 and 11 connected in series, therefore represents the sum of the instantaneous ohmic values of the two thermistors and thus the total radiant energy received by the detector 4. If the total energy received falls, the temperature of the two thermistors falls and therefore their resistance increases, producing a corresponding increase in voltage between the nodes 18 and 17, i.e. in the signal 10. The difference between the signals 10 and 9 therefore increases, to give a greater feed current intensity for the source 1, which consequently increases its emitted radiant energy to compensate the previous reduction in the energy received, to keep this latter constant and with it the voltage between the nodes 18 and 19 of the bridge 24. The analyser will therfore operate at its maximum detection capacity, and in particular at its maximum sensitivity, the value of which depends directly on the total energy received.

The radiant energy is maintained constant, as stated, by the feedback provided by the connection between the bridge 24 and differential amplifier 8. However this also leads to further advantages of the analyser according to the invention, and in particular of that shown on the drawing. One of these is represented by the fact that as the thermistor 11 of the two thermistors 11 and 12 is reached by the greater part of the radiant energy received by the detector and is therefore the thermistor more sensitive to changes in total radiant energy, once the sample has been placed between the source and detector the small unbalance of the bridge 24 usually produced during calibration (i.e. without the sample in position) to take account of any small absorption of energy of frequencies different from those of the investigated component, is automatically compensated. A further advantage is the fact that as any change in concentration of the investigated component automatically results in a change in the radiant energy received, with a corresponding change in radiant energy emitted, the usual characteristic absorption/concentration curve tends to undergo an appreciable transformation from logarithmic to linear.

What we claim is:

1. Infrared analyser for determining the presence and concentration of a specific component in a liquid or gaseous sample comprising a source of radiant energy arranged to direct an infrared radiation beam against the sample to be analysed, and a detector arranged to receive said radiation beam downstream of the sample and provide a measurement of the concentration of the component under investigation in the form of an indication of the quantity of energy of infrared frequency absorbed by the said component during passage of the radiation beam through the sample, said detector comprising two thermistors both exposed to the radiation from the sample, in the case of one of them by way of screening means arranged to produce a different ohmic response by the two thermistors when energy is absorbed by said component, said thermistors being electrically connected into a balanceable bridge circuit provided with an instrument for measuring unbalance, so that said difference in ohmic response produces an unbalance in said bridge circuit which is indicative of the quantity of energy absorbed by said component and therefore of the concentration of the component in the sample under analysis, wherein said source of radiant energy is fed by the outlet of a comparator which receives as its respective inlets a reference signal of constant value and a signal which varies as a function of the sum of the instantaneous ohmic values of the two thermistors and therefore as the total radiant energy received by the detector.

2. Analyser as claimed in claim 1, wherein said variable signal consists of the electric voltage between two nodes of said bridge circuit, between which said thermistors are connected in series.

3. Analyser as claimed in claim 1, wherein said screening means consists of an optical filter arranged to pass only a restricted band of frequencies lying within the range of the infrared frequencies absorbable by the investigated component.

* * * * *